(12) United States Patent
van Dun et al.

(10) Patent No.: US 7,777,101 B2
(45) Date of Patent: Aug. 17, 2010

(54) RESISTANCE TO PHYSIOLOGICAL DISORDERS IN LETTUCE

(75) Inventors: Cornelis Maria Petrus van Dun, Roosendaal (NL); Joyce Sylvia Velterop, Rijswijk (NL); Johannes Wilhelmus Schut, Wouw (NL); Robert Helene Ghislain Dirks, Oudenbosch (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 275 days.

(21) Appl. No.: 11/650,834

(22) Filed: Jan. 8, 2007

(65) Prior Publication Data

US 2007/0180579 A1    Aug. 2, 2007

(30) Foreign Application Priority Data

Jan. 6, 2006    (EP)    ................ 2006075040

(51) Int. Cl.
*A01H 1/00* (2006.01)
*A01H 5/00* (2006.01)
*A01H 5/10* (2006.01)
*A01H 3/00* (2006.01)
*A01G 7/00* (2006.01)

(52) U.S. Cl. ................ 800/305; 800/298; 800/295; 435/468; 435/430.1

(58) Field of Classification Search ................ None
See application file for complete search history.

(56) References Cited

U.S. PATENT DOCUMENTS

2002/0129404 A1* 9/2002 Clendennen et al. ........ 800/281

FOREIGN PATENT DOCUMENTS

WO    WO 95/01439    1/1995

OTHER PUBLICATIONS

Saltveit et al. Postharvest Biology and Technology 27 (2003) 277-283.*
Fan et al. HORTScience 35(7):1312-1314 (2000).*

Jose M. Alonso, et al., Five Components of the Ethylene-Response Pathway Identified in a Screen for Weak Ethylene-Insensitive Mutants in Arabidopsis, PNAS (2003) vol. 100. No. 5, pp. 2992-2997.
Anthony B. Bleecker, et al., Insensitivity to Ethylene Conferred by a Dominant Mutation in *Arabidopsis thaliana*, Science (1988) vol. 241, pp. 1086-1089.
Joseph R. Ecker, The Ethylene Signal Transduction Pathway in Plants, Science (1995) vol. 268, pp. 667-675.
Plinio Guzman, et al., Exploiting the Triple Response of Arabidopsis to Identify Ethylene-Related Mutants, The Plant Cell (1990) vol. 2, pp. 513-523.
Dangyang Ke, et al., Plant Homme Interaction and Phenolic Metabolism in the Regulation of Russet Spotting in Iceberg Lettuce, Plant Physiol. (1988) vol. 88, pp. 1136-1140.
Harry J. Klee, et al., Manipulation of Ethylene Synthesis and Perception in Plants: The Ins and the Outs, HortScience (2002) vol. 37, No. 3, p. 6-8.
O. Long-Fang, et al., Ethylene Insensitive and Post-Harvest Yellowing Retardation in Mutant Ethylene Response Sensor (*boers*) Gene Transformed Broccoli (*Brassica olercea* var. *italica*) Molecular Breeding (2004) vol. 14, p. 199-213.
Database Accession No. PREV200510280923: Annelies De Paepe, et al. The Arabidopsis Mutant EER2 Has Enhanced Ethylene Responses in the Light, Journal of Experimental Botany (Sep. 2005) XP-002446317.
Database Accession No. PREV200300557756: Haya Friedman, et al., Effect of Octanoic Acid on Ethylene-Mediated Processes in Arabidopsis, Plant Growth Regulation (Jul. 2003) XP-002446318.
Database Accession No. PREV200100291005: Paul B. Larsen, et al., The Arabidopsis EER1 Mutant Has Enhanced Ethylene Responses in the Hypocotyl and Stem, Plant Physiology (Feb. 2001) XP-002446319.
Ronald Pierik, et al., The Janus Face of Ethylene: Growth Inhibition and Stimulation, TRENDS in Plant Science (2006) vol. 11, No. 4, pp. 176-183.

* cited by examiner

*Primary Examiner*—Medina A Ibrahim
(74) *Attorney, Agent, or Firm*—Frommer Lawrence & Haug LLP; Thomas J. Kowalski; Heather J. DiPietrantonio

(57) ABSTRACT

Provided is a method for screening a population of plants for the presence therein of individuals that show a reduced susceptibility to ethylene and physiological disorders, in particular Russet Spotting and Yellowing, as compared to a control plant, wherein a population of seeds is germinated in darkness and in the presence of ethylene to obtain seedlings that, when having a longer hypocotyl as compared to the original ethylene-sensitive control under ethylene, are selected as plants showing a reduced susceptibility to ethylene and physiological disorders, in particular Russet Spotting or Yellowing. Also provided are plants thus selected.

20 Claims, 1 Drawing Sheet

A

B

RESISTANCE TO PHYSIOLOGICAL DISORDERS IN LETTUCE

CROSS-REFERENCE TO RELATED APPLICATIONS

This application claims priority to EP application no. 2006075040, filed Jan. 6, 2006. The foregoing application, all documents cited in the foregoing application ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The invention relates to a method for screening a population of plants for individuals that are altered with respect to their mode of ethylene response. The invention further relates to plants and plant parts, in particular leafy vegetables, thus identified. More in particular, this invention relates to lettuce (*Lactuca sativa* L.) that shows an altered response to ethylene which leads to a reduced susceptibility of this crop species to physiological disorders such as Russet Spotting and Yellowing. The invention also relates to seeds and progeny of these plants and plant parts.

BACKGROUND OF THE INVENTION

Breeding of leafy vegetables like lettuce aims at the production of commercial varieties optimally adapted to produce marketable products. Many characteristics need to be taken into account during selection which relate to both input and output traits. One of the most important traits in this respect relates to post-harvest quality, in particular to shelf life. The avoidance of physiological disorders and more in particular Russet Spotting and Yellowing are important elements that can extend the shelf life of a lettuce crop or parts thereof.

Ethylene is a plant hormone generally known to stimulate physiological processes related to senescence. In lettuce this stimulation becomes apparent through the formation of symptoms such as Russet Spotting and Yellowing.

The Russet Spotting disorder is characterised by the appearance of brown spots alongside the midrib of the leaves whereas Yellowing is the general bleaching of leaves which occurs during senescence as a consequence of chlorophyll breakdown.

Although mature heads of lettuce are known to produce only minute amounts of ethylene, the plants are highly sensitive towards this plant hormone. Therefore, physiological disorders associated with ethylene sensitivity which reduce the post-harvest quality of lettuce are mainly caused by external sources of ethylene. Exposure to such external sources can occur during harvesting, processing and storage of the produce.

For example, when lettuce is transported or stored in the vicinity of ethylene producing fruits such as apples, pears or peaches severe deterioration may occur. Furthermore, when lettuce is processed and used in packaged fresh-cut mixtures there may be limitations with respect to the ingredients which can be used due to ethylene release by one or more of the ingredients.

Russet Spotting is a physiological disorder which is manifested by the appearance of numerous brown spots along the midrib of the leaf. The browning symptoms can spread all over the leaf during the progressive stages of the disorder. Russet Spotting is known to occur especially when mature lettuce heads are stored at lower temperatures (5° C.) in the presence of low concentrations (ppm levels) of ethylene.

Symptom formation can be antagonised by applying the plant hormone auxin or calcium. Furthermore, modified atmospheres containing low oxygen levels reduce the speed at which symptoms develop.

At the biochemical level Russet Spotting appears to develop as a consequence of a local stimulation of lignin biosynthesis, which causes lignification and cell wall thickening around the area of the leaf where the visual symptoms will appear.

The brown discolouration is caused by the stimulation of phenolic metabolism. The enzyme phenylalanine ammonia lyase (PAL), which has been shown to be induced by ethylene, catalyses the first committed step of the phenylpropanoid pathway. Phenolic compounds which are formed mainly include caffeic acid derivatives as well as a number of flavonoids such as (+)catechin and (−)epicatechin. Subsequent oxidation of these compounds by polyphenol oxidase (PPO) leads to the brown discolouration typically observed in Russet Spotting. Finally, the symptoms may become more severe due to collapsing of tissue and cell death.

Senescence is a naturally occurring, developmental process at the end of a life cycle of a plant or plant organ during which metabolism is reprogrammed in order to remobilize resources into reproductive structures like seeds. Although senescence is a developmental process caused by endogenous factors like physiological age, there are many exogenous factors which can modulate senescence.

Yellowing of leaves, the most visible symptom of senescence, is a consequence of chlorophyll breakdown during a relatively late stage of senescence, which can be enhanced by ethylene once a leaf is receptive. Well-known other stimulating factors of senescence are wounding, darkness and nutrient deficiency. Although ethylene is the most important plant hormone known to stimulate senescence, other hormones like jasmonate may also contribute to this process.

From the moment of harvest of the lettuce crop until the moment of consumption, the produce can be exposed to the different exogenous factors contributing to senescence. These can be wounding during harvesting and processing, darkness and nutrient deficiency during storage and ethylene during processing and storage. These factors strongly stimulate the post-harvest disorders which can become apparent as Russet Spotting and Yellowing. Although these effects are largely cosmetic the product becomes much less attractive and thereby unmarketable.

In order to counter the deterioration effects, many post-harvest measures can be taken which reduce these effects. For example, one can store the harvested lettuce at low temperatures to retard senescence. Although this may reduce the rate of Yellowing, Russet Spotting may be enhanced. In addition, logistic measures may be implemented that reduce the transportation time required from the field to the consumer or that prevent the lettuce from being stored in the vicinity of an ethylene source. Furthermore, chemical treatments may be applied, which prevent the post-harvest deterioration, although food safety and consumer acceptance obviously become an issue.

Many of the post-harvest measures are successful to some extent but there is certainly room for improvement. Moreover, costs involved may be substantial, which is another reason to explore alternatives that reduce the need to apply post-harvest treatments. Preferably, a genetic solution is found which reduces or eliminates the need to take the expensive, preventive measures that are currently used to maintain the post-harvest quality at a high level.

It is the object of the present invention to provide a screening method to identify ethylene-insensitive plants. It is a further object of the invention to provide plants that are obtainable by the method.

SUMMARY OF THE INVENTION

This object is achieved according to the invention by a method for screening a population of plants for the presence therein of individuals that show a reduced susceptibility to ethylene and physiological disorders, in particular Russet Spotting and Yellowing, as compared to a control plant, which method comprises:

a) providing a population of seeds;

b) germinating the seeds in darkness and in the presence of ethylene to obtain seedlings;

c) selecting seedlings that show longer hypocotyls than the hypocotyls of an ethylene-sensitive control;

d) selfing the selected seedlings to produce seeds;

e) germinating one part of the seeds produced from each selected seedling in darkness and in the presence of ethylene and another part of the seeds from each selected seedling in darkness in air; and f) measuring the relative growth of the hypocotyls of the seedlings germinated under ethylene versus the growth of the hypocotyls of the seedlings germinated in air for distinguishing plants that have a longer hypocotyl as compared to the original ethylene-sensitive control both in ethylene and in air from plants that have a longer hypocotyl as compared to the original ethylene-sensitive control only under ethylene, wherein plants that have a longer hypocotyl as compared to the original ethylene-sensitive control only under ethylene are identified as plants showing a reduced susceptibility to ethylene and physiological disorders, in particular Russet Spotting or Yellowing.

The invention provides a method of identifying a plant having reduced susceptibility to a physiological disorder associated with ethylene sensitivity as compared to an ethylene-sensitive control plant, which method comprises:

a) germinating a population of seeds in darkness and in the presence of ethylene to produce seedlings;

b) selecting a seedling having elongated hypocotyls or roots as compared to a seedling of the control plant;

c) self-fertilizing the selected seeding to produce seeds;

d) germinating a portion of the seeds in darkness and in the presence of ethylene to produce S1 seedlings and germinating a portion of the seeds in darkness and in air to produce S2 seedlings; and e) comparing hypocotyls of S1 seedlings to hypocotyls of S2 seedlings and to hypocotyls of control plant seedlings;

wherein if the hypocotyls of S1 seedlings are elongated as compared to hypocotyls of S2 seedlings and control plant seedlings, a plant having reduced susceptibility to a physiological disorder associated with ethylene sensitivity as compared to a control plant is identified.

The invention is based on the hypothesis that ethylene-insensitive plants, in particular lettuce, would be resistant to post-harvest physiological disorders such as Russet Spotting and Yellowing.

In a preferred embodiment, the method of the invention comprises the further step of testing plants that have been identified in the previous steps as showing a reduced susceptibility to ethylene for their resistance to Russet spotting and/or Yellowing.

Hypocotyl length and root length can be observed by comparison to the standard and scored from 1, which means equal to the ethylene-sensitive standard variety under ethylene, to 3, which means equal to the ethylene-sensitive standard variety under air. If desired, measurements in millimeters can be made. Using one of these measurements, simple statistical analyses like a t-test, well-known to the person skilled in the art, can be performed to establish whether a plant or group of plants is significantly less sensitive to ethylene than the ethylene-sensitive standard, like cv. 'Troubadour' (Rijk Zwaan, De Lier, NL). The applied significance level of a one-sided test is 0.001.

For non-naturally occurring plants, the statistical comparison is preferably made to the hypocotyl lengths and optionally the root lengths of the original variety (i.e. the starting material) from which the non-naturally occurring plant was derived, which is the best available standard.

An ethylene-sensitive plant is a plant that shows a relatively strong response to ethylene. The relative response of a plant to ethylene can be determined by comparing phenotypic characteristics of a plant grown under ethylene versus air. Such phenotypic characteristics can be manifested in many ways including but not limited to shoot and root growth and development (so called triple response), yellowing, organ abscission, fruit ripening and relative transcript abundance of ethylene responsive genes. The strength of the relative response of a plant to ethylene depends on the specific conditions used to evoke such response, as well as on the genetic composition of the plant.

For finding ethylene-insensitive plants in existing plant material, one or more representative samples of varieties, breeding lines and/or gene bank accessions are selected. The statistical comparison is then suitably made between the hypocotyl and root lengths of the individual accession under investigation and the rest of the population. When statistically testing individuals for significantly longer hypocotyls and/or roots multiple comparison tests may be needed to maintain proper overall significance levels, for example Dunnett's multiple comparison test with one standard (Dunnett, C W, J. Amer. Statist. Assoc. 50:1096-1121 (1955)).

The plants to be screened are usually leafy vegetable plants, in particular plants belonging to the genus *Lactuca* and in particular to the species *Lactuca sativa*.

The plant population is preferably a population of non-naturally occurring plants because the chances are higher to find a plant of the invention in such variant population. However, any population of plants may be screened according to the invention.

The population of non-naturally occurring plants can comprise mutant plants, preferably obtained by a mutagenesis treatment using chemicals and/or irradiation. Mutagenesis treatments are well-known and will be further described below.

The concentration of ethylene in the initial step is at least 10 μg/liter, preferably between 11 and 25 μg/liter. The concentration of ethylene in step d) is about 4 to 5 μg/liter.

The selection step in the screening method of the invention is based on the elongation of the hypocotyls. Exposure of dark-grown germinating seedlings to ethylene causes radial swelling of the hypocotyl and inhibition of root and hypocotyl growth. This phenomenon is generally referred to as the triple response. (See, for example, Guzman, P. & Ecker, J.;

Plant Cell 2:513-523 (1990).) The reproducibility of this response allows screening for plant that show an altered triple response in the presence or absence of ethylene. In addition to or instead of measuring the elongation of the hypocotyls, the selection according to the invention may be based on one or more of the other elements of the triple response test.

According to a further aspect, the invention provides plants showing a reduced susceptibility to ethylene and physiological disorders, in particular Russet Spotting and Yellowing, as compared to a control plant, which plants are obtainable by subjecting a population of plant seeds to a screening method of the invention and selecting plants from the population that show longer hypocotyls in comparison with an ethylene-sensitive control as plants showing a reduced susceptibility to ethylene and physiological disorders, in particular Russet Spotting or Yellowing.

The plant of the invention is preferably a leafy vegetable plant, in particular a plant which belongs to the genus *Lactuca* and in particular to the species *Lactuca sativa*.

The invention further relates to plants that show a reduced susceptibility to ethylene and physiological disorders, in particular Russet Spotting or Yellowing and are obtainable by crossing a plant of the invention with another plant of the same species. The feature "reduced susceptibility to ethylene and physiological disorders, in particular Russet Spotting or Yellowing" can thus be brought into other plants that originally do not have the feature. Whether the plants resulting from such a cross are indeed plants of the invention can be tested by subjecting these plants to the screening method of the invention.

The invention further relates to progeny of a parent plant of the invention that shows reduced susceptibility to ethylene and physiological disorders, in particular Russet Spotting or Yellowing. Such progeny may be many generations removed from the parent. Provided that the feature "reduced susceptibility to ethylene and physiological disorders, in particular Russet Spotting or Yellowing" is present, the progeny plant is a plant of the invention.

The invention further relates to parts of the plants of the invention. The plant parts are for example lettuce heads or leaves, such as baby leaves, processed heads or cut leaves.

Plant parts of the invention can be used in tissue culture to regenerate plants that have reduced susceptibility to ethylene and physiological disorders, in particular Russet Spotting or Yellowing as found in the plant from which the tissue for the tissue culture is derived. Such regenerated plants are also part of this invention.

The invention further relates to seed of a plant of the invention. From the seed plants can be grown that also have the feature "reduced susceptibility to ethylene and physiological disorders, in particular Russet Spotting or Yellowing." Whether or not the seeds and thus the plants grown therefrom have retained that feature can be tested in the screening method of the invention. The invention also relates to further generation seeds that retain the reduced susceptibility to ethylene and physiological disorders, in particular Russet Spotting or Yellowing as found in the original seeds.

According to a further aspect thereof the invention relates to a vegetable product, comprising a plant or part thereof of the invention. Preferably, the vegetable is a leafy vegetable, more in particular the vegetable is lettuce.

When screened in the method of the invention, the vegetable product shows reduced susceptibility to ethylene and physiological disorders, in particular Russet Spotting or Yellowing.

It should be noted that the screening method of the invention is a relatively simple method. Plants of the invention that have a reduced susceptibility to ethylene and physiological disorders, in particular Russet Spotting or Yellowing can be identified in any variant population that is sufficiently large. It does not require undue experimentation to reproduce the invention and the plants of the invention must therefore not be construed as to be limited to the ones that are deposited.

As a result of their ethylene insensitivity, the lettuce plant material of the invention and seed derived therefrom show a strong increase with respect to their post-harvest quality especially related to the senescence associated phenomena such as Russet Spotting and Yellowing.

BRIEF DESCRIPTION OF THE DRAWINGS

In the examples reference is made to the following figure.

FIG. 1A shows a representative sample of ethylene-resistant (Ethylene R) and ethylene-sensitive control (—control) heads of the variety Troubadour. FIG. 1B shows a similar picture of the mutants derived from the variety Apache.

DETAILED DESCRIPTION OF THE INVENTION

Figure 1:
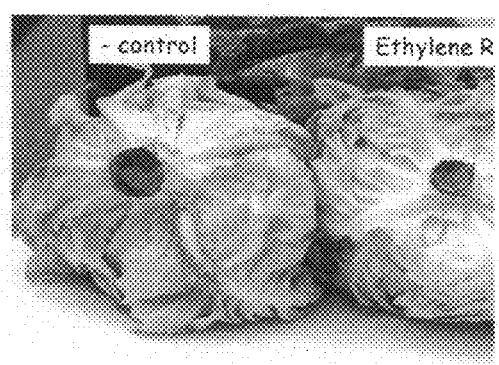
FIG. 1: Phenotype of mature heads of lettuce after exposure to ethylene at 8° C. in the dark during 9 days.
Figure 1:
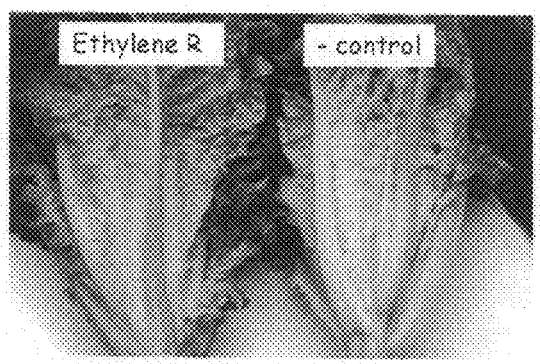

As ethylene is the most important plant hormone in stimulating senescence and as Russet Spotting and Yellowing are associated with senescence, a genetic approach was taken in which genetic variants were produced and selected for ethylene insensitivity. It was found that this indirectly leads to the identification of plants that are affected in their post-harvest senescence response.

Detailed studies using plant model species such as *Arabidopsis thaliana* as well as crop species have provided information on the biochemical pathways involved in the biosynthesis and perception of ethylene. Many allelic forms of genes have been characterised for their role in this respect providing an intricate picture of ethylene function in plants. Ethylene, like other plant hormones, plays an important role in many physiological processes embedded in complicated interactive regulatory networks.

The spatial and temporal activity of the hormone is inter alia determined at the level of gene expression underlying ethylene biosynthesis, hormone perception, signal transduction and activation of downstream effector proteins.

Allelic variants of genes involved at different levels can determine the strength of the response as well as the level of cross-talk to other signalling pathways. As ethylene biosynthesis and perception are poorly characterised in lettuce and in order to allow the identification of different response strengths and their underlying allelic variants it was reasoned that an unbiased approach may be more successful in this respect as compared to a targeted gene modification approach.

Such unbiased approach encompasses preferably a chemical or physical random mutagenesis procedure combined with an efficient phenotypic screening and selection procedure based on a response of etiolated seedlings to ethylene. Such seedling-based selection system is by far more efficient in terms of numbers of plants which can be assessed per man hour as compared to the use of mature lettuce heads. Furthermore, the time to produce plant material for screening is obviously much more reduced in the case of seedlings as compared to mature heads.

A further advantage of this approach is the use of the selection conditions at the seedling stage as predictive phenotypic marker for the post-harvest trait in consecutive generations once a successful event has been identified. A clear risk exists in the fact that selection at the seedling stage may not lead to genetic variants which express the selected trait at the mature, post-harvest level. Furthermore it is recognised that plant hormones like ethylene are involved in many physiological processes which may lead to pleitotropic effects. These can either be positive or negative depending on the crop and its cultivation conditions. The approach taken therefore preferably comprises the following steps:

1. Generation of a variant population of plants.
2. The set-up of an efficient phenotypic screen in which selection is based on a response of etiolated seedlings of plants, in particular lettuce, to ethylene which is characterised by a strong reduction of the hypocotyl elongation, a shortened, thickened root and an exaggerated apical hook curvature. This response is called the triple response which is typical for etiolated seedlings and found to occur to various degrees in many plant species when exposed to atmospheres containing ethylene. (See, for example, Ecker J., Science 268(5211):667-675 (1995).)
3. Characterisation of the plants modified in at least one test of their triple response with respect to post-harvest deterioration which comprise Russet Spotting and Yellowing. Optionally, determination of pleiotropic effects of the modification to exclude negative pleitropic effects that would affect the value of the plants.

"Variant plants" or "non-naturally occurring plants" are plants produced by human intervention. Examples of such plants are mutant plants, genetically modified plants produced, for instance, using recombinant methods, and plants resulting from intentional cross-breeding or selfing.

In the screening method of the invention the population of plant seeds to be tested is preferably a population of mutant seeds that can be obtained by a method comprising:

a) treating M0 seeds of a plant species to be modified with a mutagenic agent to obtain M1 seeds;
b) growing plants from the thus obtained M1 seeds to obtain M1 plants;
c) producing M2 seeds by self-fertilisation of M1 plant; and
d) optionally repeating step b) and c) n times to obtain M1+n seeds.

The M1+n seeds thus obtained are then germinated in darkness and in the presence of high ethylene concentration to obtain seedlings. Subsequently, seedlings are selected that do not show a response to ethylene. The response to be measured is the development of hypocotyls that are elongated as compared to the hypocotyls of an ethylene-sensitive seedling.

Then, progeny of each selected plant is split up and grown in the dark: half of the progeny under ethylene, half of the progeny under air. Relative growth of the hypocotyl under ethylene versus air is measured for each progeny under both conditions. These observations are used to distinguish progenies which have a longer hypocotyl than the original ethylene-sensitive control under ethylene, but also under air, and which can therefore be concluded to be ethylene-sensitive and not desired, from the progenies truly have a reduced susceptibility to ethylene. An example of a well-known mutagen is ems. Ems alkylates primarily G residues of a DNA strand which during DNA replication causes pairing with T instead of C. Therefore, GC basepairs change to AT basepairs at a frequency which is determined by the effective dose of ems and the activity of the mismatch repair system of the plant. The effective dose of ems depends on the concentration used, the seed size and other physical properties and the time of incubation of the seeds in the ems solution. The seeds which have been treated with ems are typically called M1 seeds. As a consequence of the treatment, the tissues of the M1 seeds contain random point mutations in the genomes of their cells and those present in the subpopulation of cells which will form the germline tissue (germinal cells) will be transferred to the next generation which is called M2. Mutations or combinations thereof which are haplo-insufficient thereby causing sterility or which induce embryo lethality will not be transferred to the M2 generation.

A similar procedure as described above for the use of ems applies for other mutagenic agents as well. The M2 population can be used in screening procedures aimed at a reduced triple response of etiolated seedlings.

Other mutagenic agents, in particular alkylating mutagenic agents, are diethyl sulfate (des), ethyleneimine (ei), propane sultone, N-methyl-N-nitrosourethane (mnu), N-nitroso-N-methylurea (NMU), N-ethyl-N-nitrosourea (enu), sodium azide.

Alternatively, the mutations are induced by means of irradiation, which is for example selected from x-rays, fast neutrons, UV irradiation.

In another embodiment of the invention the non-naturally occurring plants are produced by means of genetic engineering, such as by means of use of chimeric oligonucleotides, homologous recombination, introduction of modified target genes which compete with the endogenous product, downregulation through RNA interference, etc.

The technology to modify gene targets residing in the genome of a plant in a specific manner is known to the person skilled in the art. For example, chimeric oligonucleotides have been demonstrated to be effective mutagens with a specific mode of action. Another approach is to modify gene targets through homologous recombination or gene targeting. Using such approach, a fragment of a gene is exchanged by an introduced DNA fragment containing a desired modification. Transgenic approaches are also feasible in which modified target genes are introduced which compete with the endogenous product. This may lead to dominant negative effects. Moreover specific downregulation of the expression of genes is feasible through RNA interference.

Where mutagenic oligonucleotides, gene targeting or transgenic approaches are used to modify a genetic factor involved in ethylene function, obviously, the primary structure of the relevant genes should be known. Currently however, for lettuce knowledge on such genes is limited.

Preferably, the invention further comprises pyramiding alleles of reduced susceptibility towards ethylene.

Production of M1 and M1+n seeds is suitably effected by means of self-pollination.

The screening method of the invention may also be used to identify naturally occurring, wild type plants with the desired phenotype of reduced wound-induced discolouration. Once identified, these plants can be crossed or selfed and the non-naturally occurring progeny selected for the desired phenotype.

The invention further relates to plants or plant parts, which have in their genome genetic information which is responsible for the reduced susceptibility towards physiological disorders such as Russet Spotting and Yellowing and is found in the genome of a lettuce plant as listed in Table 1.

Progeny of the plants as claimed are also part of this invention. "Progeny" as used herein is intended to encompass all plants having the same or a similar reduced susceptibility towards ethylene and physiological disorders, in particular Russet Spotting or Yellowing, as the original plants described herein and being derived therefrom in any way, such as by sexual reproduction, such as self-fertilisation or cross-fertilisation with another plant of the same genus, or vegetative reproduction, such as cutting, tissue culture, haploid culture, protoplast culture, protoplast fusion or other techniques. Such progeny is thus the first generation of plants as identified according to the invention, as well as the first generation of plants derived by one or more of these techniques. Also included in the invention is every further generation of plants derived by one or more of these techniques, provided that the derived plants have reduced susceptibility.

To determine the response of the etiolated lettuce seedlings towards ethylene, use was made of specially designed plastic containers in which lettuce seedlings were grown on filter papers under an atmosphere in which ethylene levels can be varied. It was indeed found that the lettuce seedlings responded to the presence of ethylene by a reduced elongation of the hypocotyl, which in principle would allow selection for ethylene-insensitive variants in case such variants reside in the available population and in case the insensitivity is expressed phenotypically at the seedling level under the experimental conditions which were applied.

By growing large numbers of etiolated lettuce seedlings from a population containing randomly induced mutations under an ethylene containing atmosphere, it was found that seedlings showing reduced ethylene sensitivity as compared to the ethylene sensitivity of the starting population can be obtained and selected. Seedlings were selected showing hypocotyl elongation comparable to a situation in which the atmosphere was composed of air without ethylene. The seedlings identified in this manner were characterized as being insensitive to ethylene.

To confirm that the ethylene-insensitive variants are resistant to Russet spotting and Yellowing the variants identified in the screen are tested for their resistance to Russet spotting and/or Yellowing.

A Russet spot test suitably comprises storing harvested mature heads in a closed container at a temperature of 8° C. in the dark, and exposing them to ethylene gas at a concentration of between 6 and 7 vpm (volume parts per million) and assessing the presence of symptoms of Russet spot after 7 days, preferably after 9 days. Suitably, an ethylene-sensitive control head is incubated together with the plants to be tested and Russet spotting of the plants to be tested is compared therewith.

A Yellowing test comprises storing mature heads of the lettuce plants to be tested in an ethylene-free storage chamber at 8° C. and assessing the yellowing of the base leaves after 10 days, preferably after 14 days. Yellowing resistant plants are plants that do not show yellowing of the base leaves after 14 days. Suitably, an ethylene-sensitive control head is incubated together with the plants to be tested and the Yellowing response of the plants to be tested is compared therewith.

As illustrated in the Examples, it has been demonstrated for the first time that ethylene-insensitivity leads to resistance to Russet spotting and to resistance to Yellowing that is not induced by ethylene.

Surprisingly, seedlings which showed an elongation response which was reduced as compared to the control conditions but which were longer as compared to the sensitive controls were also found which were considered to be insensitive to ethylene as well, albeit partially.

The variable levels of ethylene insensitivity that were observed may reflect either the presence of different mutant loci or different allelic forms of identical loci affecting this trait in the original population.

In case of recessive mutation, these two possibilities can easily be distinguished by carrying out allelism assays which comprises the crossing of the two mutant events and determining the phenotype of the hybrid. In case of allelism of the mutations, the ethylene insensitivity will be apparent in the F1 whereas in case the phenotype in the mutants is determined by different recessive loci this will not be the case.

As random mutagenesis was applied as a preferred means to generate the starting population, mutations in the genetic background may also contribute to the variation of the seedling phenotype under the experimental conditions. In order to discriminate between single mutations of different strength and a combined effect of mutation in the genetic background, backcrosses should be performed to create uniform genetic backgrounds for the different ethylene-insensitive events. Such procedure is further relevant in order to determine whether mutations at specific loci involved in ethylene sensitivity display pleiotropic effects.

The M2 plants thus selected on the basis of a reduced response to ethylene were used to grow M3 seeds. In some cases M3-plants grown from the M3-seeds were selected for reduced ethylene sensitivity in a triple response test and selfed to produce M4-seeds. This was even repeated until M5 in a few cases.

In one case, an M3-plant grown from M3-seed was selected for reduced ethylene sensitivity in a triple response test, and crossed with an ethylene-sensitive and Russet spot sensitive parent to obtain F1-seed. An F1-plant grown from the F1-seed was selfed to produce F2-seeds. An F2-plant grown from these F2-seeds was selected for reduced ethylene sensitivity in a triple response test, and selfed to produce F3-seeds. This F3-line was added to the set of M3 and M4 inbred lines. Subsequently, the inbred lines descending from the ethylene-insensitive events were re-evaluated for their response to ethylene. The level of insensitivity of each inbred line was scored on the basis of the relative growth of the seedling under an ethylene containing atmosphere versus air. Based on this criterion 12/54 lines that were scored ethylene-insensitive earlier were now classified as being sensitive.

These false positives during the initial screen at the M2 level, can readily be eliminated during the re-evaluation of the events in the next generation.

The inbred lines that showed a confirmed and significant ethylene insensitivity in the ethylene test were resown and grown in a greenhouse under regular lettuce production conditions to produce mature heads that were assessed for Russet Spotting and Yellowing. (See also the Examples.)

As negative controls, ethylene-sensitive plants that originate from the population which was used to select the ethylene-insensitive events were grown. Surprisingly, the seeds of all ethylene-insensitive mutants germinated normally i.e. comparable to the seeds of a near-isogenic ethylene-sensitive control plant when planted in potting soil.

This contrasts sharply to the situation in other plant species, such as *Arabidopsis thaliana*, which show a strong reduction in germination capacity when planted in potting soil (Harpham, N. J. V. et al (1991) Annals of Botany 68, 55-61). Apparently for lettuce it is possible to grow ethylene-insensitive mutants according to a normal cultivation practice, which, in many cases, includes sowing in potting soil blocks or potting soil plugs.

After cultivation, mature heads were harvested and exposed to ethylene. One week of post-harvest incubation of heads at 8° C. under an ethylene containing atmosphere resulted in a strong induction of Russet Spotting of the heads of the ethylene-sensitive control plants. However, 29 out of 37 ethylene-insensitive events which were assessed showed no sign of Russet Spotting at all which surprisingly demonstrates that ethylene resistance which was selected for at the seedling level can reduce physiological disorders at the mature plant level, even at the post-harvest stage.

Yellowing resistance could be demonstrated for a number of ethylene-insensitive events under ethylene-free storage conditions at sub-optimal temperature. This is surprising, because until now Yellowing resistance has only been reported in the presence of ethylene. (Saltveit et al., Postharvest Biology and Technology 27:277-283 (2003).)

With the screening method of the invention, ethylene-insensitive mutants were identified and selected. Seeds of these mutants were deposited under the terms of the Budapest Treaty with NCIMB Ltd., Ferguson Building, Craibstone Estate, Bucksburn, Aberdeen AB21 9YA UK on 3 Jan. 2007 and have been given the accession numbers listed in Table 1. Deposited seeds will be irrevocably and without restriction or condition released to the public during the term of any patent issued from this application. Details about seed descendance of the deposits are given in Example 3 and in Example 4. These deposits are made because they have the single specific characteristic of significantly reduced susceptibility to ethylene. They were not tested for DUS-criteria for variety registration, i.e. distinguishability, uniformity, stability on all registration characteristics, and are not expected to meet these criteria in any way.

TABLE 1

| Plant no. | Internal ref. (=NCIMB ref.) | NCIMIB accession number |
|---|---|---|
| 00D.7856 | 07D.826509 | 41449 |
| 00D.6876 | 07D.826514 | 41450 |
| 00D.7871 | 07D.826502 | 41448 |
| 00D.6883 | 07D.826522 | 41451 |
| 00D.6896 | 07D.826540 | 41452 |
| 00D.7845 | 07D.826542 | 41453 |

The present invention will be illustrated in the Examples that follow and that are not intended to limit the invention in any way. More in particular, the experiments in the Examples are performed with lettuce but the invention is more broadly applicable to other plant species that encounter similar post-harvest difficulties when contacted with ethylene.

EXAMPLES

Example 1

Genetic Modification of Lettuce by Ethyl Methane Sulfonate (ems)

Seeds of the lettuce varieties Troubadour, Apache and Yorvik (all from Rijk Zwaan, De Lier, The Netherlands) were treated with ems by submergence of approximately 2000 seeds per variety into an aerated solution of either 0.05% (w/v) or 0.07% (w/v) ems during 24 hours at room temperature.

Approximately 1500 treated seeds per variety per ems dose were germinated and the resulting plants were grown in a greenhouse in the Netherlands from May to September to produce seeds.

After maturation, M2 seeds were harvested and bulked in one pool per variety per treatment. The resulting 6 pools of M2 seeds were used as starting material to identify the individual M2 plants containing reduced susceptibility alleles.

The efficacy of the genetic modification procedure was assessed by determining the occurrence of bleached plants, which is indicative for chlorophyll loss due to modifications in genes directly or indirectly involved in the formation or accumulation of chlorophyll. In all 6 pools of M2 seeds individual plants, which are bleached, were observed which demonstrates that the applied treatments result in genetic modifications.

Example 2

Identification of Lettuce Plants which have Obtained Reduced Susceptibility Alleles for Ethylene M2 lettuce seeds were germinated on paper in a small plastic container with an ethylene concentration of 10 20 vpm (volume parts per million) at 16° C. in dark. 1 vpm contains 0.41 µmol/liter or 1.14 µg/liter. Ethylene-insensitive mutants were compared to ethylene-sensitive controls, and selected on the basis of elongated hypocotyl and/or root (i.e. triple response test). These ethylene-insensitive mutants were grown to produce M3 lines by self fertilisation. These M3 lines were re-tested with the triple response test to confirm ethylene insensitivity.

When a line was segregating for ethylene insensitivity, plants were selected followed by one or two additional cycles of inbreeding, and a final triple response test to select homozygous ethylene-insensitive lines, if possible.

In one case, an M3-plant grown from M3-seed was selected for reduced ethylene sensitivity in a triple response test, and crossed with an ethylene-sensitive and russet spot sensitive parent Troubadour to obtain F1-seed. An F1-plant grown from the F1-seed was selfed to produce F2-seeds. An F2-plant grown from these F2-seeds was selected for reduced ethylene sensitivity in a triple response test, and selfed to produce F3-seeds. The resulting F3-line was added to the set of 53 M3, M4, and M5 inbred lines. In this case the F3-line was the only representative of the original M2-mutant plant, because there were no selfed seeds left from this plant.

This set of 54 M3 and M4 lines from Example 1 were germinated on peat blocks in a closed container under ethylene concentration between 4 and 4.5 vpm in the dark. Ethylene-insensitive mutants were identified by their longer hypocotyls in comparison with sensitive control varieties (Troubadour, Apache, Yorvik, Sensai). Results are presented in Table 1. 42 Out of 54 lines that were identified by the triple response test appeared to be at least partial ethylene-insensitive in the ethylene test. These lines represent 40 M2 plants because two M2 plants were represented twice. Table 2 shows the results.

TABLE 2

Ethylene response of mutant lines in a closed container test and a triple reponse test (TRT). Observations on hypocotyl and root are indicated separately, when no consistent response is shown. Intermediate response is indicated as partial.

| Plot | Seed no. | Origin | Ethylene | TRT |
|---|---|---|---|---|
| 1. | Yorvik | | S | S |
| 2. | Troubadour | | S | S |
| 3. | Apache | | S | S |
| 4. | 00D.88531 | Y | S | R/S hypo; R root |
| 5. | 00D.88539 | Y | S | S |
| 6. | 01D.85717 | Y | S | R |
| 7. | 01D.85720 | Y | S | R |
| 8. | 01D.85732 | Y | S | S |
| 9. | 00D.88533 | Y | S | S |
| 10. | 00D.88538 | Y | S | R |
| 11. | 03D.74008 | Y | R | S |
| 12. | 02D.90749 | Y | S | S |
| 13. | 00D.88550 | Y | S | S |
| 14. | 01D.85739 | Y | S | S |

TABLE 2-continued

Ethylene response of mutant lines in a closed container test and a triple reponse test (TRT). Observations on hypocotyl and root are indicated separately, when no consistent response is shown. Intermediate response is indicated as partial.

| Plot | Seed no. | Origin | Ethylene | TRT |
|---|---|---|---|---|
| 15. | 00D.88565 | T | R | R |
| 16. | 02D.91445 | T | R | R |
| 17. | 00D.88577 | T | R/S | R hypo; S root |
| 18. | 02D.91446 | T | R | R |
| 19. | 02D.91447 | T | R | R |
| 20. | 01D.85754 | T | S? | R/S |
| 21. | 02D.90047 | T | R | R |
| 22. | 01D.85758 | T | R | R |
| 23. | 00D.88564 | T | S | S |
| 24. | 02D.91442 | T | R | R |
| 25. | 00D.88569 | T | R | R |
| 26. | 00D.88573 | T | R | R |
| 27. | 00D.88578 | T | R | R |
| 28. | 00D.88582 | T | R | R |
| 29. | 01D.85748 | T | R/S | R/S |
| 30. | 01D.85750 | T | S | R |
| 32. | 01D.85755 | T | R/S | R/S |
| 33. | 01D.85762 | A | Partial R | R hypo; S root |
| 34. | 03D.90452 | A | R | R |
| 35. | 01D.85764 | A | Partial R/S | R hypo; S root |
| 36. | 02D.90070 | A | R | R |
| 37. | 03D.90457 | A | R | R |
| 38. | 01D.85768 | A | R | R |
| 39. | 02D.90128 | A | R | R |
| 40. | 02D.90129 | A | R | R |
| 41. | 02D.90130 | A | R | R |
| 42. | 03D.90462 | A | R | R |
| 43. | 03D.90464 | A | R | R |
| 44. | 02D.90133 | A | R | R |
| 45. | 02D.90134 | A | R | R |
| 46. | 00D.88600 | A | R/S | R |
| 47. | 02D.91479+ | A | R | R |
| 48. | 01D.85772 | A | R | S hypo; R root |
| 49. | 04D.800957 | A | R | S hypo; R root |
| 50. | 02D.90091 | A | R | R |
| 51. | 04D.800960 | A | R | S hypo; R root |
| 52. | 04D.800963 | A | R | R |
| 53. | 01D.85780 | A | R | R |
| 54. | 01D.85756 | T | R | R |
| 55. | 02D.90036 | T | Partial R | S hypo; R root |
| 56. | 04D.801660 | Y | Partial R | R/S hypo; S root |
| 58. | 04D.800900 | T | R | S hypo; R root |
| 59. | 03D.90323 | T | R | R |
| 60. | Sensai | S | S | |

R = ethylene-insensitive;
S = ethylene-sensitive;
R/S = segregating;
T = Troubadour;
A = Apache;
Y = Yorvik;
hypo = hypocotyl

Example 3

Identification of Lettuce Plants which have Obtained Reduced Susceptibility Alleles for Russet Spot Thirty-seven ethylene-insensitive lines from the forty-two lines found in Example 2 were sown in a greenhouse to produce mature heads under regular lettuce production conditions (location: Maasdijk, the Netherlands; sowing on day 1, transplanting on day 39, harvesting on day 99). The harvested mature heads were stored in a closed container at a temperature of 8° C. in the dark. They were exposed to ethylene gas at a concentration of between 6 and 7 vpm (volume parts per million). One vpm contains 0.41 μmol/liter or 1.14 μg/liter. After 9 days, plants displaying Russet Spotting were identified. All control plants, except Yorvik displayed Russet Spotting. 29 Out of 37 lines tested showed absence of Russet Spotting or less Russet Spotting as compared to the original variety (Table 3).

Six lines were chosen for multiplication and deposit at NCIMB Ltd, Ferguson Building, Craibstone Estate, Bucksburn, Aberdeen AB21 9YA, UK. The first line is numbered 02D.91445. It is an M4-line descending from the ethylene-insensitive Troubadour-M2-plant 00D.7856. An ethylene-insensitive M4-plant was selected from 02D.91445 in the closed container test in Example 2 and selfed to produce M5-seeds. Sixteen M5-plants were grown from these seeds to produce an M6 seed lot by selfing. This seed lot is numbered 07D.826509 and is deposited as NCIMB-number 41449 (first line).

The second line is numbered 02D.90047. It is an M4-line descending from the ethylene-insensitive Troubadour-M2-plant 00D.6876. An ethylene-insensitive M4-plant was selected from 02D.90047 in the closed container test in Example 2 and selfed to produce M5-seeds. Sixteen M5-plants were grown from these seeds to produce an M6 seed lot by selfing. This seed lot is numbered 07D.826514 and is deposited as NCIMB-number 41450 (second line). The absence of russet spotting for this origin was established by testing the M5-line 03D.90323, descending from an M4-plant of 02D.90047.

The third line is numbered 00D.88578. It is an M3-line descending from the ethylene-insensitive Troubadour-M2-plant 00D.7871. Sixteen M3-plants were grown from the 00D.88578 to produce an M4 seed lot by selfing. This seed lot is numbered 07D.826502 and is deposited as NCIMB-number 41448 (third line).

The fourth line is numbered 03D.90452. It is an M5-line descending from the ethylene-insensitive Apache-M2-plant 00D.6883. An ethylene-insensitive M5-plant was selected from 03D.90542 in the closed container test in Example 2 and selfed to produce M6-seeds. Sixteen M6-plants were grown from these seeds to produce an M7 seed lot by selfing. This seed lot is numbered 07D.826522 and is deposited as NCIMB-number 41451 (fourth line).

The fifth line is numbered 01D.85780. It is an M3-line descending from the ethylene-insensitive Apache-M2-plant 00D.6896. An ethylene-insensitive M3-plant was selected from 01D.85780 in the closed container test in Example 2 and selfed to produce M4-seeds. Sixteen M4-plants were grown from these seeds to produce an M5 seed lot by selfing. This seed lot is numbered 07D.826540 and is deposited as NCIMB-number 41452 (fifth line).

The sixth line is numbered 04D.801660. It is an F3-line descending from a cross between the ethylene-insensitive Yorvik-M3-plant 02D.8484 and a plant of the ethylene-sensitive variety Troubadour. The M3-plant 02D.8484 descended from the ethylene-insensitive Yorvik-M2-plant 00D.7845. An ethylene-insensitive F3-plant was selected from 04D.801660 in the closed container test in Example 2 and selfed to produce F4-seeds. Sixteen F4-plants were grown from these seeds to produce an F5 seed lot by selfing. This seed lot is numbered 07D.826542 and is deposited as NCIMB-number 41453 (sixth line).

FIG. 1 shows resistant and control plants.

Example 4

Identification of Lettuce Plants that Show Less Post-Harvest Yellowing

Ethylene-insensitive lines grown under greenhouse conditions as described for Example 3 were harvested and mature trimmed heads were stored in a ethylene free storage chamber at 8° C. After two weeks base leaves of the green control varieties Yorvik and Troubadour started to turn yellow. At that moment and even 1 week later three lines appeared to have less yellow base leaves than their origin varieties, which were the controls used in this trial. These lines were numbered 04D.800900, 03D.90323, 04D.801660. Although a relationship is reported between leaf yellowing and ethylene presence (Saltveit et al. (2003) Postharvest Biology and Technology 27:277 283), it is surprising that even in conditions without ethylene, some of the ethylene-insensitive lines are expressing a less yellowing phenotype.

TABLE 3

Observations of russet spotting on mature heads after 9 days of storage in ethylene conditions.

| Seed no. | Ethylene | TRT | Russet Spot |
|---|---|---|---|
| 01D.85762 | Partial R | R hypo; S root | 2 |
| 03D.90452 | R | R | 0 |
| 01D.85764 | R/S | R hypo; S root | 1 |
| 02D.90070 | Partial R | R | 0 |
| 03D.90457 | R | R | 0 |
| 01D.85768 | R | R | 0 |
| 02D.90128 | R | R | 2 |
| 02D.90129 | R | R | 2 |
| 02D.90130 | R | R | 2 |
| 03D.90462 | R | R | 2 |
| Apache | S | S | 2 |
| 03D.90464 | R | R | 0 |
| 02D.90133 | R | R | 2 |
| 02D.90134 | R | R | 2 |
| 00D.88600 | R/S | R | NA |
| 02D.91479 | R | R | 0 |
| 01D.85772 | R | S hypo; R root | 0 |
| 04D.800957 | R | S hypo; R root | 0 |
| 02D.90091 | R | R | 0 |
| 04D.800960 | R | S hypo; R root | 0 |
| 04D.800963 | R | R | 2 |
| 01D.85780 | R | R | 0 |
| Apache | S | S | 2 |
| 00D.88565 | R | R | 0 |
| 02D.91445 | R | R | 0.5 |
| 00D.88577 | R/S | R hypo; S root | 0 |
| 02D.91446 | R | R | 0 |
| 02D.91447 | R | R | 0 |
| 01D.85754 | S? | R/S | 0 |
| 01D.85756 | R | R | 0 |
| 02D.90047 | R | R | NA |
| 01D.85758 | R | R | 0 |
| 02D.91442 | R | R | 0 |
| Troubadour | S | S | 1 |
| 00D.88569 | R | R | 0 |
| 00D.88573 | R | R | 0 |
| 00D.88578 | R | R | 0 |

TABLE 3-continued

Observations of russet spotting on mature heads after 9 days of storage in ethylene conditions.

| Seed no. | Ethylene | TRT | Russet Spot |
|---|---|---|---|
| 00D.88582 | R | R | 0 |
| 01D.85748 | R/S | R/S | 0/1 |
| 02D.90036 | Partial R | S hypo; R root | NA |
| 01D.85755 | R/S | R/S | NA |
| 04D.800900 | R | S hypo; R root | 0.5 |
| 03D.90323 | R | R | 0 |
| 04D.801660 | Partial R | R/S hypo; S root | 0/2 |
| Yorvik | S | S | 0 |

0 = symptoms absent;
1 = weak symptoms;
2 = strong symptoms;
NA = not available

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

We claim:

1. A non-naturally occurring lettuce plant, or part thereof, identified by:
    a) germinating a population of seeds in darkness and in the presence of ethylene to produce seedlings;
    b) selecting a seedling having elongated hypocotyls or roots as compared to a seedling of a control plant;
    c) self-fertilizing the selected seedling to produce seeds;
    d) germinating a portion of the seeds in darkness and in the presence of ethylene to produce S1 seedlings and germinating a portion of the seeds in darkness and in air to produce S2 seedlings; and
    e) comparing hypocotyls of S1 seedlings to hypocotyls of S2 seedlings and to hypocotyls of control plant seedlings,
    wherein the hypocotyls of S1 seedlings of the plant are elongated as compared to hypocotyls of S2 seedlings and control plant seedlings, and
    wherein the plant has reduced susceptibility to ethylene and Russet Spotting and Yellowing as compared to an ethylene-sensitive control plant,
    representative seeds of which having been deposited under NCIMB accession number 41449, NCIMB accession number 41450, NCIMB accession number 41448, NCIMB accession number 41451, NCIMB accession number 41442, or NCIMB accession number 41453.

2. The plant of claim 1, wherein the plant part is a leaf, a head, a cut leaf, a baby leaf or a processed head.

3. A seed of the plant of claim 1.

4. A seed deposited with NCIMB having an accession number selected from the group consisting of: i) accession number 41449, ii) accession number 41450, iii) accession number 41448, iv) accession number 41451, v) accession number 41452, and vi) accession number 41453.

5. A non-naturally occurring plant, or part thereof, produced from the seed of claim 4, having reduced susceptibility to ethylene and Russet Spotting and Yellowing as compared to an ethylene-sensitive control plant.

6. A lettuce plant, or part thereof, produced by propagation of and/or breeding with the non-naturally occurring plant of claim 5, and having reduced susceptibility to ethylene and Russet Spotting and Yellowing.

7. The plant, or part thereof of claim 1, wherein said part of the plant is suitable for sexual reproduction.

8. The plant, or part thereof of claim 7, said part is selected from the group consisting of microspores, pollen, ovaries, ovules, embryo sacs and egg cells.

9. The plant, or part thereof of claim 1, wherein said part of the plant is suitable for vegetative reproduction.

10. The plant, or part thereof of claim 9, said part is selected from the group consisting of cuttings, roots, stems, cells, protoplasts, leaves, meristems and buds.

11. A tissue culture produced from the lettuce plant of claim 1.

12. The tissue culture as claimed in claim 11, wherein said tissue culture is produced from a tissue selected from the group consisting of leaves, pollen, embryos, cotyledon, hypocotyls, meristematic cells, roots, root tips, anthers, flowers, seeds and stems.

13. A non-naturally occurring plant of *Lactuca sativa*, or part thereof, having reduced susceptibility to ethylene and Russet Spotting and Yellowing, representative seeds of which having been deposited under NCIMB accession number 41449, NCIMB accession number 41450, NCIMB accession number 41448, NCIMB accession number 41451, NCIMB accession number 41442, or NCIMB accession number 41453.

14. A seed of the plant of claim 13.

15. A non-naturally occurring plant of *Lactuca sativa*, or part thereof, having reduced susceptibility to ethylene and Russet Spotting and Yellowing, representative seeds of which having been deposited under NCIMB accession number 41449, NCIMB accession number 41450, NCIMB accession number 41448, NCIMB accession number 41451, NCIMB accession number 41442, or NCIMB accession number 41453, said plant grown from the seed as claimed in claim 14.

16. A non-naturally occurring plant of *Lactuca sativa*, or part thereof, having reduced susceptibility to ethylene and Russet Spotting and Yellowing, representative seeds of which having been deposited under NCIMB accession number 41449, NCIMB accession number 41450, NCIMB accession number 41448, NCIMB accession number 41451, NCIMB accession number 41442, or NCIMB accession number 41453, said plant regenerated from the part of the plant as claimed in claim 15.

17. A tissue culture of the plant of claim 13.

18. A non-naturally occurring plant of *Lactuca sativa*, or part thereof, having reduced susceptibility to ethylene and Russet Spotting and Yellowing, representative seeds of which having been deposited under NCIMB accession number 41449, NCIMB accession number 41450, NCIMB accession number 41448, NCIMB accession number 41451, NCIMB accession number 41442, or NCIMB accession number 41453, said plant regenerated from the tissue culture as claimed in claim 17.

19. A method of producing a lettuce plant, or part thereof, having reduced susceptibility to ethylene and Russet Spotting and Yellowing, comprising producing progeny from a non-naturally occurring plant of Lactuca sativa, or part thereof, having reduced susceptibility to ethylene and Russet Spotting and/or Yellowing, representative seeds of which having been deposited under NCIMB accession number 41449, NCIMB accession number 41450, NCIMB accession number 41448, NCIMB accession number 41451, NCIMB accession number 41442, or NCIMB accession number 41453; wherein said progeny have reduced susceptibility to ethylene and Russet Spotting and Yellowing.

20. A lettuce plant produced from the method of claim 19, having reduced susceptibility to ethylene and Russet Spotting and Yellowing.

* * * * *